United States Patent [19]

Brown

[11] Patent Number: 4,870,177

[45] Date of Patent: Sep. 26, 1989

[54] IMPROVED PROCESS FOR PRODUCING PURE BORONIC AND BORINIC ESTERS

[75] Inventor: Herbert C. Brown, West Lafayette, Ind.

[73] Assignee: Aldrich-Boranes, Inc., Milwaukee, Wis.

[21] Appl. No.: 134,514

[22] Filed: Dec. 17, 1987

Related U.S. Application Data

[62] Division of Ser. No. 902,176, Aug. 29, 1986, Pat. No. 4,772,751.

[51] Int. Cl.$^4$ .............................................. C07F 5/04
[52] U.S. Cl. ...................................... 546/13; 549/213; 558/298
[58] Field of Search ......................... 558/298; 546/13; 549/213

[56] References Cited

PUBLICATIONS

Brown, Herbert C. et al., Organometallics 1983, 2, pp. 1316–1319.
Brown, Herbert C. et al., Organometallics 1985, 4, pp. 1788–1792.

*Primary Examiner*—Donald B. Moyer
*Assistant Examiner*—Karen E. Kulesza
*Attorney, Agent, or Firm*—Joyce R. Niblack

[57] ABSTRACT

Improved processes for liberating boronic, RB(OR')$_2$, and borinic, RR'BOR', esters from their "ate" complexes, free of alcohol are provided. Pyrolysis of lithium organylborates LiRB(OR')$_3$ and LiRR'BOR', wherein R is an organyl group and R' is straight or branched-chain lower alkyl, directly yields the relatively volatile boronic and borinic esters in high purity, leaving behind a residue of lithium alkoxide. Treatment of the lithium organylborates with an appropriate acid halide cleanly liberates either volatile or non-volatile boronic or borinic esters, readily separated from the lower alkyl ester produced as a by-product. The novel compound lithium dimethylborohydride is also provided.

4 Claims, No Drawings

IMPROVED PROCESS FOR PRODUCING PURE BORONIC AND BORINIC ESTERS

This is a division of application Ser. No. 902,176, filed Aug. 29, 1986, now U.S. Pat. No. 4,772,751, issued Sept. 20, 1988.

BACKGROUND OF THE INVENTION

It is well known that the reaction of lithium alkyls or aryls with methyl or ethylborate resulted in the formation of mixtures of products.

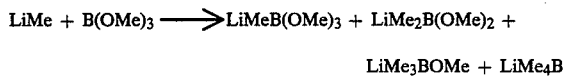

$$LiMe + B(OMe)_3 \longrightarrow LiMeB(OMe)_3 + LiMe_2B(OMe)_2 + LiMe_3BOMe + LiMe_4B$$

This presented a serious problem in the synthesis of pure boronic and borinic esters $RB(OR')_2$ and $R_2BOR'$.

I discovered that the problem could be overcome by a careful choice of the boronic or borinic ester used. Esters of secondary alcohols with boronic acid or borinic acids gave essentially quantitative yields of a single product. [H. C. Brown and T. E. Cole, *Organometallics*, 2, 1316-19 (1983); H. C. Brown, T. E. Cole and M. Srebnik, *Organometallics*, 4, 1788-92 (1985).]. For reasons of availability and cost, isopropyl alcohol is the preferred secondary alcohol.

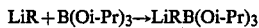
$$LiR + B(Oi\text{-}Pr)_3 \rightarrow LiRB(Oi\text{-}Pr)_3$$

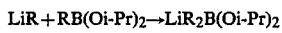
$$LiR + RB(Oi\text{-}Pr)_2 \rightarrow LiR_2B(Oi\text{-}Pr)_2$$

In order to liberate the desired boronic ester or borinic ester from the complex, acids such as sulfuric acid or hydrogen chloride were used.

$$LiRB(Oi\text{-}Pr)_3 + HCl \rightarrow LiCl + RB(Oi\text{-}Pr)_2 + i\text{-}PrOH$$

$$LiR_2B(Oi\text{-}Pr)_2 + HCl \rightarrow LiCl + R_2BOi\text{-}Pr + i\text{-}PrOH$$

In practice, it was discovered that these by-product alcohols often form azeotropes with the desired boronic and borinic esters, $RB(Oi\text{-}Pr)_2$ and $R_2BOi\text{-}Pr$, azeotropes which greatly complicate separation of the alcohols and the esters. These alcohols interfere with the subsequent use of these boronic and borinic esters for the synthesis of lithium alkyl-substituted borohydrides [B. Singaram, T. E. Cole and H. C. Brown, *Organometallics*, 3, 774-777 (1984); B. Singaram, T. E. Cole and H. C. Brown, *Organometallics*, 3, 1522-25 (1984)].

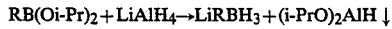
$$RB(Oi\text{-}Pr)_2 + LiAlH_4 \rightarrow LiRBH_3 + (i\text{-}PrO)_2AlH \downarrow$$

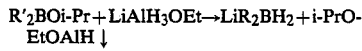
$$R'_2BOi\text{-}Pr + LiAlH_3OEt \rightarrow LiR_2BH_2 + i\text{-}PrO\text{-}EtOAlH \downarrow$$

The presence of free alcohol in the boronic and borinic esters results in the formation of difficulty separable mixtures.

The present invention overcomes the difficulties of the prior art processes and provides two improved procedures for liberating boronic, $RB(OR')_2$, and borinic, $RB'BOR$, esters from their "ate" complexes, free of alcohol.

SUMMARY OF THE INVENTION

In one embodiment, the present invention provides a process for producing borinic and boronic esters in high purity comprising the steps of pyrolysis of lithium organylborates, $LiRB(OR')_3$ and $LiRR'B(OR'')_2$ under reduced pressure and separating the resulting boronic and borinic esters, $RB(OR')_2$ and $R_2BOR'$ from the lithium alkoxide residue according to the Formulae I and II:

$$LiRB(OR')_3 \xrightarrow{\Delta, \text{vac}} RB(OR')_2 + LiOR' \qquad (I)$$

$$LiR_2B(OR')_2 \xrightarrow{\Delta, \text{vac}} R_2BOR' + LiOR' \qquad (II)$$

wherein R is an organyl group, R' is straight or branched chain lower alkyl or cycloalkyl and B is boron.

This process has major advantages for the preparation of relatively volatile boronic and borinic esters, completely free of alcohol.

In a second embodiment of this invention, the process comprises the steps of treating a lithium mono- or diorganylborate with an appropriate acid halide, and separating the organic ester by-product by distillation. Such esters do not normally form azeotropes with boronic or borinic esters and can readily be separated from these products by distillation. The process of the second embodiment of this invention is represented by Formulae III and IV:

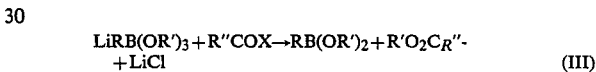
$$LiRB(OR')_3 + R''COX \rightarrow RB(OR')_2 + R'O_2CR'' + LiCl \qquad (III)$$

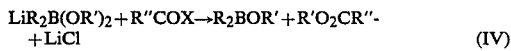
$$LiR_2B(OR')_2 + R''COX \rightarrow R_2BOR' + R'O_2CR'' + LiCl \qquad (IV)$$

wherein R is an organyl group, R' and R'' are straight or branched chain lower alkyl and may be the same or different, and X is halo.

As used herein, the term "straight or branched chain lower alkyl" refers to alkyl groups having from 3 to 6 carbon atoms such a n-propyl, isopropyl, n-butyl, isobutyl, tert-butyl, n-pentyl, 3-methyl-2-butyl, and the like.

The term cycloalkyl refers to an organic radical containing a saturated $C_3$–$C_6$ carbon ring from which one hydrogen atom has been removed.

As used herein, the term "halo" refers to chloro, fluoro, iodo and bromo.

The term "organyl", as used herein, refers to a substituted or unsubstituted, cyclic or acyclic (straight or branched chain) organyl group.

The term "aryl", as used herein, refers to an organic radical derived from an aromatic hydrocarbon by the removal of one hydrogen atom.

The term "heterocyclic" refers to an organic radical derived from a heterocyclic system by the removal of one carbon atom, such as furyl, piperidinyl, and the like.

For reasons of availability and economy, isopropyl alcohol is the preferred secondary alcohol, and thus R' in the above reaction schemes is preferrably isopropyl (i-Pr).

The preferred acid halides are acetyl and benzoyl halides.

In the event the ester, for example, isopropyl acetate, boils too closely to the desired boronic or borinic ester, a shift to benzoyl chloride provides the much less volatile isopropyl benzoate, facilitating the separation by distillation. Even less volatile acid halides, such as 3,4- dichlorobenzoyl chloride, can be utilized to given an even greater spread in boiling point.

Acid bromides may also be employed, however, for reasons of economy, acid chlorides are preferred.

This procedure greatly facilitates the synthesis of lithium mono- and diorganylborohydrides containing organic groups of low molecular weight, i.e., groups having from 1 to 8 carbon atoms such as methyl, ethyl, n-propyl, isopropyl, n-butyl, isobutyl, tert-butyl, n-pentyl, 3-methyl-2-butyl, and the like.

The synthesis of these valuable products, such as lithium methylborohydride, is represented by the following reaction schemes.

Similarly, dimethylborohydride can be synthesized as follows:

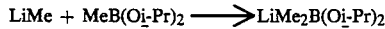

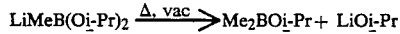

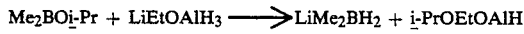

The above processes for the synthesis of boronic and borinic esters are widely applicable. Lengthening of the chain from methyl to n-butyl is satisfactory. Branching the chain to, for example, isopropyl, sec-butyl, tert-butyl and the like is satisfactory. Cycloalkyl groups such as cyclopentyl and cyclohexyl can be utilized. Aromatic groups such as phenyl, toluyl, anisyl and naphthyl groups, etc. and heterocyclic groups such as 2-furyl can be accomodated.

In a third embodiment of the present invention, which works satisfactorily only for the methyl derivative, dimethylborinic acid "ate" complex can be treated directly with lithium alkoxyaluminumhydride to form the disubstituted borohydride.

This method works satisfactorily only for the methyl derivatives.

DETAILED DESCRIPTION OF PREFERRED EMBODIMENTS

The following examples further illustrate the present invention. In the following examples, all glassware was dried at 140° C. for at least three hours and assembled hot under a stream of nitrogen. Reactions were carried out under a static pressure of nitrogen. Anhydrous ethyl ether Mallinckrodt) was stored over 4 Å molecular sieves under nitrogen and used without further purification. The organolithium reagents are commercial materials (Aldrich or Alfa), except for isopropyllithium, which was prepared according to the method of Gilman, H.; Moore, F. W.; Baine, O., *J. Am. Chem. Soc.*, 1941, 63, 2479. The concentrations were standardized prior to use, but the reagents were not purified further. Triisopropoxyborane, acetyl chloride and benzoyl chloride (Aldrich) were distilled from calcium hydride and stored under nitrogen. $^1$N NMR spectra were recorded on a Varian T-60 spectrometer, relative to tetramethylsilane; $^{11}$B NMR spectra were recorded on a Varian FT-80 spectrometer (25.517 MHz) relative to boron trifluoride etherate. Mass spectra were obtained on a Finnigan Model 4000 gas chromatographic mass spectrometer. Microanalyses were performed in house.

EXAMPLE 1

General Procedure for the Thermal Dissociation of Lithium Organyltriisopropylborates and Lithium Diorganyldiisopropoxyborates The following preparation of methyl diisopropoxyborane is typical. A 50 mL round-bottom flask containing a magnetic stirring bar and connected to a cold trap fitted with 2 stopcocks (closed) into which were placed loose wads of glass wool (to filter out lithium isopropoxide fines), and a sidearm capped with a rubber septum was charged with triisopropoxyborane (9.81 g, 52.2 mmol) and 52 mL ethyl ether. The flask was cooled to −78° C. (acetone, dry ice) and methyllithium (37.3 mL, 52.2 mmol) was slowly added via a double-ended needle. During the addition, a white precipitate formed. Stirring was continued for an additional hour at −78° C., then for 2 hours at ambient temperature. The outlet of the cold trap was connected to a water aspirator, the stopcocks opened and vacuum slowly applied so as to prevent frothing. After 2 h, the aspirator was replaced by a high vacuum pump (0.2 mm Hg) and residual ethyl ether removed. The reaction flask was immersed in an oil bath and the cold trap cooled to −78° C. The reaction mixture was heated (110°–120° C. oil bath temperature) under vacuum (0.1–0.2 mm Hg) for 3 h. During this time the flask was occasionally shaken to insure proper stirring and heat transfer. The oil bath was removed, the stopcocks closed, and the cold trap filled with nitrogen. After warming to room temperature, the methyl diisopropoxyborane collected in the cold trap was transferred via a double-ended needle to a vial. Yield: 6.8 g (47.2 mmol, 90%). Proton NRM (neat) δ 4.30 (septet, J=18 Hz, 2H), 1.05 (d, J=18 Hz, 12H), 0.08 (bs, 3H); boron NMR (neat) δ+30.3 ppm (s). Methyl diisopropoxyborane has been prepared in 500 mmol-runs in the same proportions as described above, with yields up to 96%.

EXAMPLE 2

Preparation of Isopropyldiisopropoxyborane

The title compound was prepared following the procedure of Example 1, from isopropyllithium (177 mL, 101 mmol) and triisopropoxyborane (19.0 g, 101 mmol). Solvent was removed at 0° C. and 15 mm Hg. The oil bath was heated to 80° C. Yield: 16.3 g (94.2 mmol, 93%), bp 138° C. (749 mm Hg); $n^{20}D$ 1.3853; proton NMR (CDCl$_3$) δ 4.40 (septet, J=18 Hz, 2H); 1.13 (d, J=18 Hz, 12H), 0.93 (bs, 7H); boron NMR (neat)δ+30.5 ppm (s). Anal. Calcd. for $C_9H_{21}BO_2$: C, 62.80; H, 12.22; B, 6.29. Found: C, 62.59; H, 12.59; B, 5.93.

EXAMPLE 3

Preparation of n-Butyldiisopropoxyborane

Following the method of Example 1, reaction of n-butyllithium (115 mL, 218 mmol) and triisopropoxyborane (41 g, 218 mmol) yielded n-butyldiisopropoxyborane, 37.3 g, (291 mmol, 93%). Proton NMR (neat) δ 4.20 (septet, J=18 Hz, 2H), 1.23–0.63 (m, 9H) overlap with isopropyl doublet at 0.98 (d, J=18 HZ, 12H); boron NMR (neat)δ+30.2 ppm (s).

EXAMPLE 4

Preparation of sec-Butyldiisopropoxyborane

Following the method of Example 1, reaction of sec-butyllithium (208 mL, 250 mmol) and triisopropoxyborane (47.0 mL, 250 mmol), with solvents removed at 0° C. and 15 mm Hg and oil bath temperature maintained at 50° C., yielded sec-butyldiisopropoxyborane, 42.0 g (206 mmol, 90%), bp 138°–140° C. (754 mm Hg); proton NMR (neat) δ 4.35 (septet, J=18 Hz, 2H), 1.09 (d, J=18 Hz, 12H), 0.8 (bm, 9H); boron NMR (neat)δ+79.5 ppm (s).

EXAMPLE 5

Preparation of tert-Butyldiisopropoxyborane

The reaction was conducted as described in Example 1 with tert-butyllithium (30.9 mL, 51 mmol) which was added to triisopropoxyborane (9.59 mL, 51 mmol) in 51 mL ethyl ether cooled to −100° C. instead of −78° C. Solvents were removed at 0° C. and 15 mm Hg. The oil bath was maintained at 50° C. to furnish tert-butyldiisopropoxyborane: 8.44 g (45.3 mmol, 89%), bp 136°–138° (754 mm Hg); proton NMR (neat)δ+4.50 (septet, J=18 Hz, 2H), 1.12 (d, J=18 Hz, 12H), 0.95 (s, 9H); boron NMR (neat) δ+29.5 ppm (s).

EXAMPLE 6

Preparation of Phenyldiisopropoxyborane

This reaction was conducted following the procedure described in Example 1 using phenyllithium (57 mL, 102 mmol) to yield phenyldiisopropoxyborane, 18.0 g (97.3 mmol, 86%), proton NMR (neat) δ 7.93 (m, 2H), 7.57 (m, 3H), 4.6 (septet, 2H), 1.10 (d, 12H); boron NMR (neat) δ+28 ppm (s).

EXAMPLE 7

Preparation of tert-Butylmethylisopropoxyborane

The reaction was run following the procedure described in Example 1 using methyllithium (38.4 mmol, 24.6 mL) and tert-butyldiisopropoxyborane (7.15 g, 38.3 mmol). Volatiles were removed at atmospheric pressure and the product distilled to yield 3.9 g (27.5 mmol, 73%), bp 90°–92° C. (741 mm Hg); proton NMR (CDCl$_3$) δ 4.30 (septet, J=18 Hz, 1H), 1.15 (d, J=18 Hz, 6H), 0.83 (s, 9H), 0.30 (brs, 3H); boron NMR (neat) δ+52.9 ppm (s).

EXAMPLE 8

Preparation of Dimethylisopropoxyborane

Following the method of Example 1, methyllithium (50 mmol, 42 mL) and methyldiisopropoxyborane (7.1 g, 50 mmol) were reacted. The workup was conducted as described in Example 1, using an oil bath temperature of 80° C. to yield dimethylisopropoxyborane, 4.6 g (46 mmol, 92%), proton NMR (CDCl$_3$) δ 4.40 (septet, J=18 Hz, 1H), 1.19 (d, J=18 Hz, 6H), 0.37 (brs, 6H): boron NMR (neat) δ+52.1 ppm (s).

Table I summarizes the thermal decomposition of representative lithium organyltriisopropoxyborates and lithium diorganyldiisopropoxyborates.

TABLE I

Thermal Decomposition of Lithium Organyltriisopropoxyborates and Lithium Diorganyldiisopropoxyborates

| lithium borate | temp for thermal decomp °C. | borate | scale mmol | yield % isolated |
|---|---|---|---|---|
| methyltriisopropoxy- | 120 | methyldiisopropoxy- | 50–500 | 91–96 |
| isopropyltriisopropoxy- | <25 | isopropyldiisopropoxy- | 100 | 95 |
| n-butyltriisopropoxy- | 120 | n-butyldiisopropoxy- | 218–250 | 92–95 |
| sec-butyltriisopropoxy- | <25 | sec-butyldiisopropoxy- | 50–250 | 90–96 |
| tert-butyltriisopropoxy- | <25 | tert-butydiisopropoxy- | 50 | 89 |
| phenyltriisopropoxy- | 120 | phenyldiisopropoxy- | 100 | 86 |
| dimethyldiisopropoxy- | 50 | dimethylisopropoxy- | 38 | 92 |
| tert-butylmethyldiisopropoxy- | <25 | tert-butylmethylisopropoxy- | 50 | 73 |

EXAMPLE 9

General Procedure for the Decomposition of Lithium Organyl and Diorganylborates with Acid Chlorides The preparation of diphenylisopropoxyborane is typical. To a solution of phenyldiisopropoxyborane (9.0 g, 43.9 mmol) in 44 mL ethyl ether cooled to −78° C. was slowly added phenyllithium (22 mL, 44 mmol). The reaction was stirred at −78° C. for 2 h, then warmed to 0° C. Neat acetyl chloride (3.43 mL, 48.4 mmol) was added via syringe and the ice bath removed. After stirring for 15 min at room temperature, the precipitated lithium chloride was allowed to settle. The clear liquid phase and washings (2×15 mL ethyl ether) were transferred to a flat distillation flask. Volatiles were removed in vacuo. Distillation furnished pure diphenylisopropoxyborane. Yield: 8.56 g (38.3 mmol, 87%); bp 88°–90° C. (0.1 mm Hg); proton NMR (CDCl$_3$) δ 7.57 (m, 2H), 7.37 (m, 3H), 4.57 (septet, J=18 Hz, 1H), 1.25 (d, J=18 Hz, 6H); boron NMR (neat) δ+44.8 ppm (s).

EXAMPLE 10

Preparation of 2-Furyldiisopropoxyborane

Following the procedure of Example 9, 2-furyldiisopropoxyborane was prepared using 2-furyllithium, prepared by the method of Ramanathan, V.; Levine, R., *J. Org. Chem.*, 1962, 27, 1216, from furan (200 mmol, 15 mL) and n-butyllithium (200 mmol, 77 mL) and triisopropoxyborane (17.5 g, 93 mmol). The "ate" complex was treated with acetyl chloride (7.85 g, 100 mL). Isolation yielded 2-furyldiisopropoxyborane: 13.5 g (69 mmol, 74%); bp 76°–78° C. (15 mm Hg), $n^{20}D$ 1.4306; proton NMR (CDCl$_3$) δ 7.60 (m, 1H), 6.97 (m, 1H), 4.83 (septet, J=18 Hz, 2H), 1.33 (d, J=18 Hz, 12H); boron (neat) δ+23.3 ppm (s).

EXAMPLE 11

Preparation of Phenylisopropylisopropoxyborane

The reaction was conducted following the general procedure of Example 9 using isopropyllithium (22.8 mmol, 40 mL) and phenyldiisopropoxyborane (4.64 g, 22.5 mmol). Workup with acetyl chloride (1.96 g, 25 mmol) and isolation yielded 3.60 g of title compound (18.9 mmol, 84%), bp 106°–108° C. (15 mm Hg); proton NMR (CDCl$_3$) δ 7.27 (m, 5H), 4.47 (septet, J=18 Hz, 1H), 1.22 (d, J=18 Hz, 6H), 1.02 (bd, J=15 Hz, 6H); boron NRM (neat) δ+48.6 ppm (s).

EXAMPLE 12

Preparation of Dimethylisopropoxyborane

The reaction was conducted following as described under the general procedure of Example 9 using methyldiisopropoxyborane (15.3 g, 106 mmol) and methyllithium (66.3 mL, 106 mmol). The reaction was quenched with benzoyl chloride (14.9 g, 106 mmol) to yield, after careful distillation, 8.7 g (87 mmol, 82%), bp 52°–54° C. (7.58 mm Hg); proton NMR (CDCl$_3$) δ 4.40 (septet, J=18 Hz, 1H), 1.19 (d, J=18 Hz, 6H), 0.37 (bs, 6H); boron NMR (neat) δ+52.1 ppm (s).

EXAMPLE 13

Preparation of Phenyldiisopropoxyborane

Following the procedure of Example 9, phenyllithium (17 mL, 30.6 mmol) and triisopropoxyborane (5.6 g, 30 mmol) were reacted, and the reaction quenched with acetyl chloride (2.1 mL, 30 mmol) to yield after distillation 5.2 g (25.2 mmol, 84%).

The decomposition of representative lithium organyl- and diorganylborates with acid chlorides is summarized in Table II.

EXAMPLE 14

Preparation of Lithium Methylborohydride

A 2-L round-bottom flask fitted with a sidearm capped with a rubber septum and containing a mechanical stirrer was charged with 500 mmol of triisopropoxyborane (94.0 g) in 500 mL of diethyl ether. The solution was cooled to −78° C. with a dry ice/acetone bath. Methyllithium (500 mmol, 357 mL in ether) was slowly added via a double-ended needle. After the addition was complete, the reaction solution was stirred for 2 h at 78° C. The clear solution was then brought to room temperature. The outlet of the cold trap was connected to a water aspirator, the stopcocks opened, and vacuum slowly applied so at to minimize frothing. After 2 h, the aspirator was replaced by a high vacuum pump (0.2 mm Hg) and the residual ethyl ether removed. The reaction flask was immersed in an oil bath and the receiver flask cooled to −78° C. The reaction mixture was heated (110°–120° C. oil bath temperature) under vacuum (0.1–0.2 mm Hg) for 3 h. The yield was essentially quantitative. To the methyldiisopropoxyborane in the flask at 0° C. was added 500 mL of ether, followed by a 1.0M solution of 500 mmol of LiAlH$_4$ in ether. The mixture was stirred for an additional 15 min at 0° C., then allowed to warm to room temperature. The reaction mixture was filtered through a filter chamber. The clear supernate was transferred via double-ended needle to a 1-L round-bottom flask. The resultant precipitate was washed with ether (2×100 mL), filtering after each wash, and combined with the previous fraction. The volatiles were removed first at aspirator pressure, then at high vacuum to give a highly viscous liquid. This was treated with pentane (500 mL) and left in the cold room for 24 h. The residual aluminum salts were filtered off and the pentane removed in vacuo. The solid LiMeBH$_3$ was dissolved in approximately 480 mL to give a 1M solution.

The above procedure can be employed to convert all of the monoorganylboronic esters, RB(OR′)$_2$, into the corresponding borohydrides, LiRBH$_3$.

EXAMPLE 15

Preparation of Lithium Dimethylborohydride

A 500 mL round bottom flask fitted with a side-arm capped with a rubber septum and containing a magnetic stirring bar, was charged with 100 mmol of methyldiisopropoxyborane (14.4 g) in 100 mL of diethyl ether. The solution was cooled to −78° C. using a dry-ice/acetone bath. Methyllithium (100 mmol, 71.4 mL in ether) was slowly added via a double-ended needle. After the addition was complete, the reaction solution was stirred for

TABLE II

| | Decomposition of Lithium Organyl- and Diorganylborates with Acid Chlorides | | | | |
|---|---|---|---|---|---|
| lithium borate | acid chloride | borane | $^{11}$B NMR ppm | bp °C. (mmHg) | isolated yield % |
| phenyltriisopropoxy- | acetyl | phenyldiisopropoxy- | 28.0 | 98–100(8) | 84 |
| 2-furyltriisopropoxy- | acetyl | 2-furyldiisopropoxy- | 23.3 | 76–78(15) | 74 |
| dimethyldiisopropoxy- | benzoyl | dimethylisopropoxy- | 52.0 | 52–54(758) | 82 |
| phenylisopropyldiisopropoxy- | acetyl | phenylisopropoxyisopropoxy- | 48.6 | 106–108(15) | 84 |
| diphenyldiisopropoxy- | acetyl | diphenylisopropoxy- | 44.8 | 88(0.1) | 87 |

2 h at −78° C. It was then heated to dissociate the complex into dimethylisopropoxyborane, as previously described. The borinic ester was dissolved in ethyl ether and then slowly added via double-ended needle to a suspension of LiOEtAlH$_3$ prepared from ethyl acetate (50 mmol) and LiAlH$_4$ (100 mmol) at 0° C. This mixture was stirred for an additional 15 min at 0° C. then allowed to warm to room temperature. The reaction mixture was transferred via needle to a 250 mL centrifuge bottle. The clear supernate was transferred via double-ended needle to a 250 mL round-bottom flask. The resultant precipitate was washed with ether (2×25 mL), centrifuging after each wash, and combined with the previous fractions. The volatile materials were removed under reduced pressure (0.1 mm Hg) leaving a thick viscous residue which was triturated with pentane (100 mL). The residual aluminum salts were allowed to settle and the clear solution transferred to another 250 mL flask. The volatiles were removed under reduced pressure. This solid material was then dissolved in an appropriate solvent; pentane, ether or tetrahydrofuran, to make 100 mL of solution. The concentration was estimated by hydrolysis.

This general procedure can be utilized to synthesize various borinic acids, R$_2$BOR' or RR'BOR', and then converted into the corresponding borohydrides, LiR$_2$BH$_2$ or LiRR'BH$_2$.

EXAMPLE 16

Preparation of Lithium Dimethylborohydride (Compact Method)

A 500-mL round-bottom flask fitted with a side-arm capped with a rubber septum and containing a magnetic stirring bar, was charged with 100 mmol of methyldiisopropoxyborane (14.4 g) in 100 mL of diethylether. The solution was cooled to −78° C. after using a dry-ice-/acetone bath. Methyllithium (100 mmol, 71.4 mL in ether) was slowly added via a double-ended needle. After the addition was complete, the reaction solution was warmed to room temperature, then slowly added via a double-ended needle to a suspension of LiEtOAlH$_3$ prepared from ethyl acetate (50 mmol) and LiAlH$_4$ (100 mmol) at 0° C. This mixture was stirred for an additional 15 min at 0° C. then allowed to warm to room temperature. The reaction mixture was transferred via needle to a 250 mL centrifuge bottle. The clear supernate was transferred via double-ended needle to a 250 mL round-bottom flask. The resultant precipitate was washed with ether (2×25 mL) centrifuging after each wash, and combined with the previous fractions. The volatile materials were removed under reduced pressure (0.1 mm Hg) leaving a thick, viscous residue which was triturated with pentane (100 mL). The residual aluminum salts were allowed to settle and the clear solution transferred to another 250 mL flask. The volatiles were removed under reduced pressure. This solid material was then dissolved in an appropriate solvent: pentane, ether or tetrahydrofuran, to make 100 mL of solution. The concentration was estimated by hydrolysis.

As can be seen from the above examples, thermal dissolution of lithium organylalkoxyborates provides a simple, convenient, economical and superior means of obtaining boronic and borinic esters in high purity and high yields on a preparative scale. Nonvolatile boronic and borinic esters can be obtained cleanly by treatment of their respective lithium "ate" complexes with volatile acid halides, such as acetyl chloride. Volatile boronic and borinic esters can be similarly isolated using less volatile acid chlorides, such as, benzoyl chloride. The processes of the present invention provide distinct advantages over the prior art in the use of isolation for a large variety of these important boronic and borinic ester derivatives.

The above description has been given by way of illustration. It will be understood by those skilled in the art that modifications may be made without departing from the spirit and scope of the claimed invention.

The invention claimed is:

1. A process for synthesizing a pure boronic or borinic ester represented by the formulae RB(OR')$_2$ and R$_2$BOR', respectively, wherein R is an alkyl group and R' is lower alkyl or cycloalkyl, comprising the steps of reacting a lower alkyl borate with a lithium alkyl or cycloalkyl compound to form a lithium alkylborate represented by the formulae LiRB(OR')$_3$ or LiR$_2$B(OR')$_2$ wherein R and R' are as defined above; heating said lithium borate complex to a temperature of from 110°–120° C. under vacuum, to produce said ester and LiOR', and recovering said ester by cooling the reaction to a temperature of about −78° C., warming the reaction to room temperature, and thereafter separating said ester from the reaction products.

2. The process of claim 1 wherein R' is isopropyl.

3. A process for synthesizing a pure boronic or borinic ester represented by the formulae RB(OR')$_2$ and R$_2$BOR', respectively, wherein R is an alkyl, cycloalkyl, aryl or heterocyclic group and R' is lower alkyl, comprising the steps of: reacting a lower alkyl borate with a lithium alkyl, cycloalkyl, aryl or heterocyclic group to form a lithium borate complex represented by the formulae LiRB(OR')$_3$ or LiR$_2$B(OR')$_2$, respectively, wherein R and R' are as defined above; reacting said complex with an acid halide to produce the ester, R'O$_2$CR" and LiCl wherein R' and R" are the same or different members of the group consisting of alkyl, cycloalkyl, aryl or heterocyclic; and thereafter separating said ester from the reaction products by fractional distillation to obtain the pure boronic or borinic ester.

4. The process of claim 3 wherein water is added following distillation to obtain a pure boronic or borinic acid.

* * * * *